US009952156B2

(12) United States Patent
Boss et al.

(10) Patent No.: US 9,952,156 B2
(45) Date of Patent: Apr. 24, 2018

(54) NATIVE FLUORESCENCE IMAGING DIRECT PUSH PROBE

(71) Applicant: The United States of America as represented by the Secretary of the Navy, San Diego, CA (US)

(72) Inventors: Pamela A. Boss, San Diego, CA (US); Michael D. Putnam, San Diego, CA (US); Gregory W. Anderson, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/788,141

(22) Filed: Jun. 30, 2015

(65) Prior Publication Data
US 2017/0003224 A1   Jan. 5, 2017

(51) Int. Cl.
G01V 5/00   (2006.01)
G01N 21/64   (2006.01)
G01N 33/24   (2006.01)

(52) U.S. Cl.
CPC ......... G01N 21/6456 (2013.01); G01N 33/24 (2013.01); G01N 2201/062 (2013.01); G01N 2201/06113 (2013.01)

(58) Field of Classification Search
CPC ... G01V 5/02; G01V 8/02; G01V 5/06; G01T 1/178; G01T 5/10
See application file for complete search history.

(56) References Cited

U.S. PATENT DOCUMENTS

| 5,128,882 A * | 7/1992 | Cooper ................... E21B 49/00 250/253 |
| 5,604,582 A * | 2/1997 | Rhoads ................. G01J 3/2823 250/458.1 |
| 5,639,956 A | 6/1997 | Christy |
| 6,115,061 A | 9/2000 | Lieberman et al. |

(Continued)

OTHER PUBLICATIONS

Lotfabad et al. "Characterization of Contaminated Soils Using Confocal Laser Scanning Microscopy and Cryogenic-Scanning Electron Microscopy", Environ. Sci. Technol. 2000, 34, p. 3408-3414.*

(Continued)

*Primary Examiner* — David Porta
*Assistant Examiner* — Mamadou Faye
(74) *Attorney, Agent, or Firm* — SPAWAR Systems Center Pacific; Kyle Eppele; Young Fei

(57) ABSTRACT

An apparatus comprising: a direct push probe configured to be pushed into a subsurface soil environment; a transparent window mounted to a side of the probe; a white light source mounted within the probe and positioned such that when the white light source is activated only white light exits the window; an ultraviolet (UV) light source mounted within the probe and positioned such that when the UV light source is activated only UV light having a given wavelength exits the window; and an imaging system disposed within the probe and configured to capture a white-light-only-illuminated image and a UV-light-induced-fluorescence image of the subsurface soil environment at a given depth, wherein the imaging system comprises a longpass filter to filter out the UV light having the given wavelength.

9 Claims, 6 Drawing Sheets

(56) References Cited

U.S. PATENT DOCUMENTS

| | | |
|---|---|---|
| 6,630,947 B1 | 10/2003 | Lieberman et al. |
| 6,820,701 B1 | 11/2004 | Clark et al. |
| 7,319,522 B2 | 1/2008 | Havard et al. |
| 8,872,136 B1* | 10/2014 | Jackson ............... A01M 21/00 250/492.1 |
| 9,222,880 B2* | 12/2015 | Smith .................... G01N 21/27 |
| 2004/0011965 A1* | 1/2004 | Hodgkinson .......... G01N 21/64 250/461.1 |
| 2007/0046289 A1* | 3/2007 | Troxler ................. G01N 33/42 324/334 |
| 2007/0242265 A1* | 10/2007 | Vessereau ........... E21B 47/0002 356/241.1 |
| 2008/0063998 A1* | 3/2008 | Liang .................. A61B 1/0638 433/29 |
| 2008/0192246 A1* | 8/2008 | Neiss ....................... G01J 3/02 356/301 |
| 2009/0105605 A1 | 4/2009 | Abreu |
| 2010/0024535 A1* | 2/2010 | Maeda ..................... E02D 1/02 73/84 |
| 2010/0036261 A1* | 2/2010 | Weinberg ............ A61B 5/0059 600/476 |
| 2010/0257920 A1* | 10/2010 | Lee ........................ E02D 1/022 73/84 |
| 2013/0260441 A1* | 10/2013 | Fowler .................... C12N 1/20 435/255.2 |
| 2014/0301617 A1* | 10/2014 | Shida ................ A61B 1/00009 382/128 |
| 2015/0185196 A1 | 7/2015 | Coram et al. |
| 2015/0192488 A1 | 7/2015 | Xu et al. |
| 2015/0363914 A1* | 12/2015 | Boyle ............... G06F 17/30268 345/629 |
| 2016/0072991 A1 | 3/2016 | Dinev |
| 2017/0148842 A1 | 5/2017 | Feng et al. |

OTHER PUBLICATIONS

Rousseau et al. "Use of Laser Induced Fluorescence (LIF), Use of Laser Induced Fluorescence (LIF), Soil/LNAPL Laboratory Testing, Modeling Soil/LNAPL Laboratory Testing, Modeling and Actual Recovery Data to Evaluate and Actual Recovery Data to Evaluate LNAPL Mobility, Stability and Recoverability" RemTech 2006-Banff, Alberta, p. 1-41.*

R. Bhartia et al.; "Label-Free Bacterial Imaging with Deep-UV-Laser-Induced Native Fluorescence"; Appl. Environ. Microbiol., 76, 7231 (2010).

Gemain, Randy Dakota Technologies; New Generation Optical Sensors for Characterizing NAPL Source Zones; available online at http://www.dakotatechnologies.com; Spring 2008.

Henning Buddenbaum et al., "Laboratory imaging spectroscopy of soil profiles," Journal of Spectral Imaging, May 5, 2011, pp. 1-5, vol. a2 (2011), IM Publications LLP.

G. Andreoli et al., "Hyperspectral Analysis of Oil and Oil-Impacted Soils for Remote Sensing Purposes," European Commission Directorate General Joint Research Centre, Mar. 2007, pp. 1-36, EUR 22739 EN.

* cited by examiner

NATIVE FLUORESCENCE IMAGING DIRECT PUSH PROBE

FEDERALLY-SPONSORED RESEARCH AND DEVELOPMENT

The United States Government has ownership rights in this invention. Licensing and technical inquiries may be directed to the Office of Research and Technical Applications, Space and Naval Warfare Systems Center, Pacific, Code 72120, San Diego, Calif., 92152; voice (619) 553-5118; ssc_pac_t2@navy.mil. Reference Navy Case Number 102530.

BACKGROUND OF THE INVENTION

Geochemical and microbiological conditions vary tremendously over small distances in the Earth's subsurface and these variations are not captured well by current site characterization technologies. Better characterization techniques at smaller scales are needed.

SUMMARY

Described herein is a fluorescence probe comprising, consisting of, or consisting essentially of a direct push probe, a transparent window, a white light source, an ultraviolet (UV) light source, and an imaging system. The direct push probe may be configured to be pushed into a subsurface soil environment. The transparent window may be mounted to a side of the probe. The white light source may be mounted within the probe and positioned such that when the white light source is activated only white light exits the window. The UV light source may be mounted within the probe and positioned such that when the UV light source is activated only UV light having a given wavelength exits the window. The imaging system may be disposed within the probe and configured to capture a white-light-only-illuminated image and a UV-light-induced-fluorescence image of the subsurface soil environment at a given depth. The imaging system may comprise a longpass filter to filter out the UV light having the given wavelength.

The fluorescence probe may be used to obtain fluorescence imaging by completing the following steps. The first step provides for penetrating a subsurface soil environment to a given depth with a direct push probe. The next step provides for illuminating through a window in the probe the subsurface soil adjacent to the probe at the given depth with white light. The next step provides for recording, in-situ and in real time, a first image of the white-light-illuminated subsurface soil at the given depth. The next step provides for illuminating through the window the subsurface soil adjacent to the probe at the given depth with only ultra violet (UV) light such that fluorescence is excited in microbes and minerals that may be present in the subsurface soil at the given depth. The next step provides for recording, in-situ and in real time, a second image of the UV-light-illuminated subsurface soil at the given depth after the UV excitation light has been filtered from the second image such that only the fluorescence response is recorded. The next step provides for superimposing the second image over the first image to create a composite image of the subsurface soil.

DETAILED DESCRIPTION OF EMBODIMENTS

The disclosed methods and systems below may be described generally, as well as in terms of specific examples and/or specific embodiments. For instances where references are made to detailed examples and/or embodiments, it should be appreciated that any of the underlying principles described are not to be limited to a single embodiment, but may be expanded for use with any of the other methods and systems described herein as will be understood by one of ordinary skill in the art unless otherwise stated specifically.

Figure 1A:
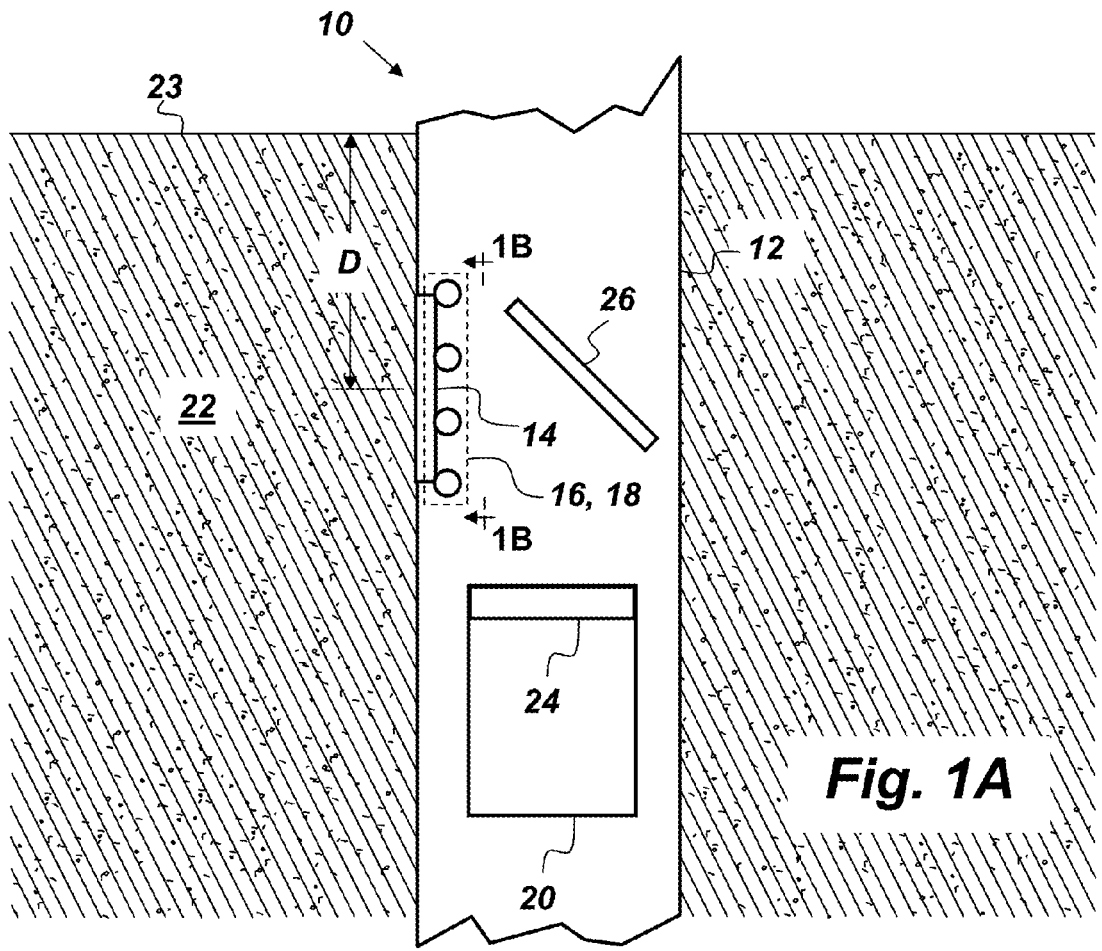
FIG. 1A is a cross-sectional side view of an embodiment of a fluorescence probe.
Figure 1B:
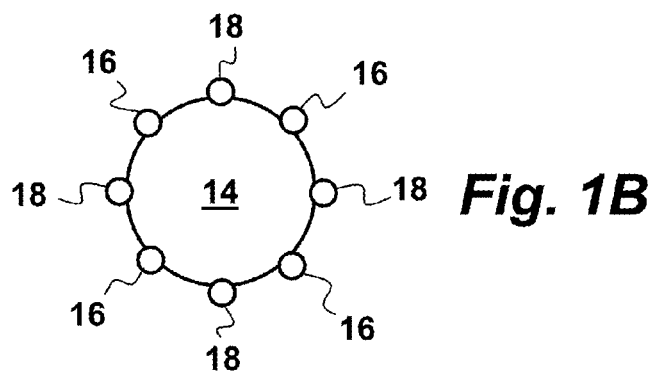
FIG. 1B is a sectional view of a transparent window and light sources.

FIGS. 1A and 1B depict an embodiment of a fluorescence probe 10 that comprises, consists of, or consists essentially of a direct push probe 12, a transparent window 14, a white light source 16, an ultraviolet (UV) light source 18, and an imaging system 20. FIG. 1A is a cross-sectional side-view of the fluorescence probe 10. FIG. 1B is a sectional view of the window 14 and the white and UV light sources 16 and 18. The direct push probe 12 may be configured to be pushed into a subsurface soil environment 22. The transparent window 14 may be mounted to a side of the probe 12. The white light source 16 may be mounted within the probe 12 and positioned such that when the white light source 16 is activated only white light exits the window 14. The UV light source 18 may be mounted within the probe 12 and positioned such that when the UV light source 18 is activated only UV light having a given wavelength exits the window 14. The imaging system 20 may be disposed within the probe 12 and configured to capture a white-light-only-illuminated image and a UV-light-induced-fluorescence image of the subsurface soil environment 22 at a given depth D from a surface 23. The imaging system 20 may comprise a longpass filter 24 to filter out the UV light having the given wavelength. In the embodiment of the fluorescence probe 10 shown in FIG. 1B, the imaging system 20 further comprises a mirror 26 positioned so as to direct light reflected off the subsurface soil environment 22 to the longpass filter 24.

The push probe 12 may be any probe capable of being pushed into the subsurface soil environment 22. The push probe 12 may be any desired size or shape. A suitable example of the push probe 12 includes, but is not limited to, a cone penetrometer such as is used in cone penetration testing (CPT).

The window 14 may be made of any transparent material. Suitable examples of the transparent window 14 include, but are not limited to, windows made of sapphire, UV grade fused silica, and quartz. Sapphire is scratch resistant. The window 14 may be attached to a side of the push probe 12 by any suitable means. In one example embodiment, the window 14 is epoxied to a window housing in the side of the push probe 12.

The white light source 16 may be any source of light capable of producing white light. Light sources that produce broad spectrum white light are preferable. A suitable example of the white light source 16 includes, but is not limited to, light emitting diodes (LEDs).

The fluorescence probe 10 may be used in any subsurface soil environment 22 that the push probe 12 may be pushed into. For example, the push probe 12 may be pushed into subsurface soil environments 22 comprising clays, sand, and sediment. Rocks can cause problems (break the window or keep one from pushing the probe deeper).

Figure 2:
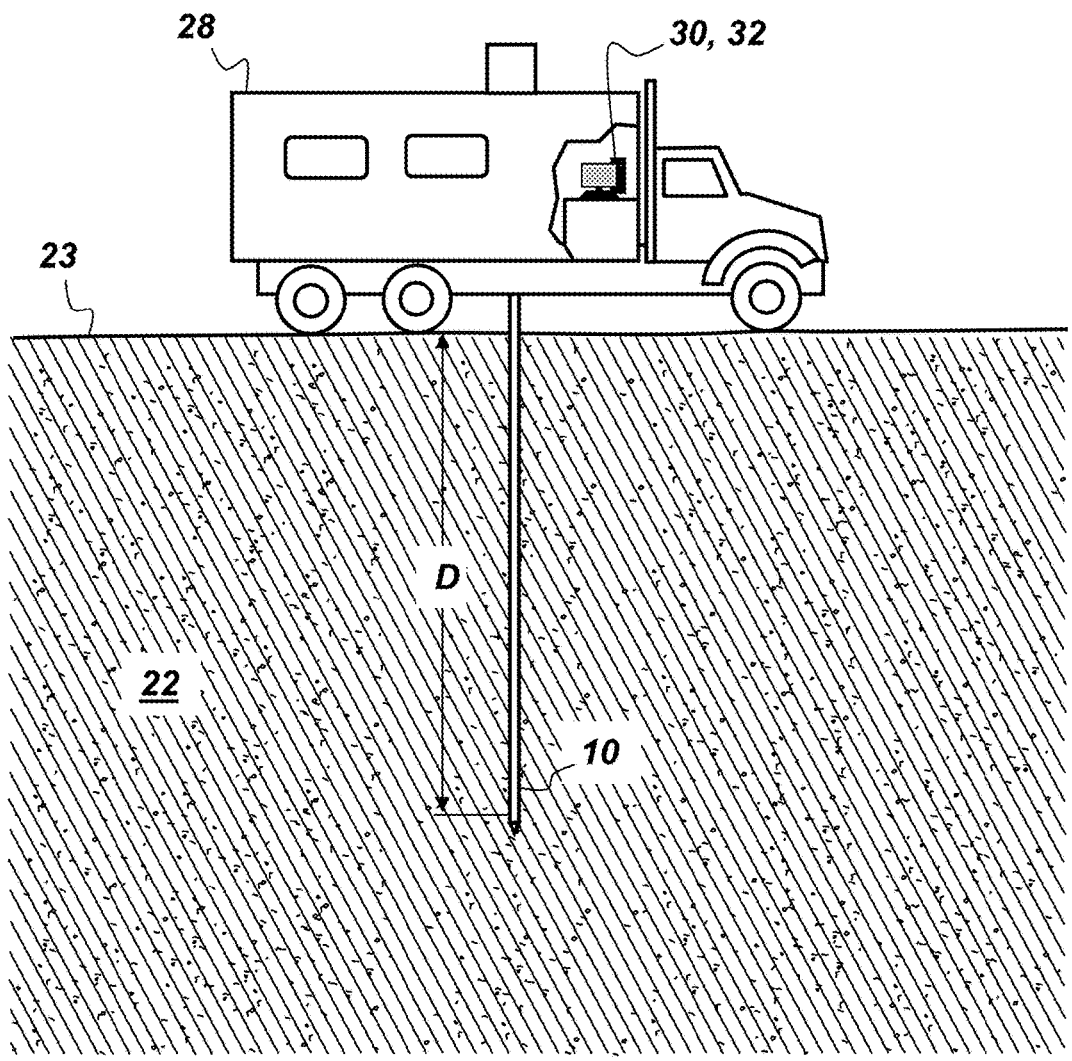
FIG. 2 is a side view illustration of an embodiment of the fluorescence probe.

FIG. 2 is a side view illustration of an embodiment of the fluorescence probe 10 where the fluorescence probe 10 is integrated into a cone penetrometer. In FIG. 2, a CPT truck 28 is shown parked on the surface 23 at a given location where the fluorescence probe 10 has been driven into the subsurface soil environment to depth D. The fluorescence probe 10 may optionally comprise a global positioning system (GPS) sensor 30 and a depth sensor 32. In the embodiment of the fluorescence probe 10 shown in FIG. 2, the GPS sensor 30 and the depth sensor 32 are mounted within the CPT truck 28. From its position at depth D, the fluorescence probe 10 is configured to obtain native fluorescence images of the subsurface soil environment 22. These images can be used to assess microbiological conditions in the soil profile as a function of depth. The fluorescence probe 10 may be used to obtain native fluorescence images at any desired depth, limited by only by the probe 12's depth capability. For example, the probe 12 may be pushed to depths exceeding 2 meters. In some cases, the probe may be pushed to depths exceeding 60 meters.

The fluorescence probe 10 may be used to quantify natural attenuation capacity of the subsurface soil environment 22, to assess and manage the spatial variability of geochemical and microbiological conditions, and to delineate the contaminants in low-permeability zones. The fluorescence imaging provided by the fluorescence probe 10 provides data on microbial activity with high vertical and horizontal spatial resolution necessary to determine the biogeochemical processes that are occurring in the subsurface. The imaging data are obtained in-situ and in real-time.

Figure 3:
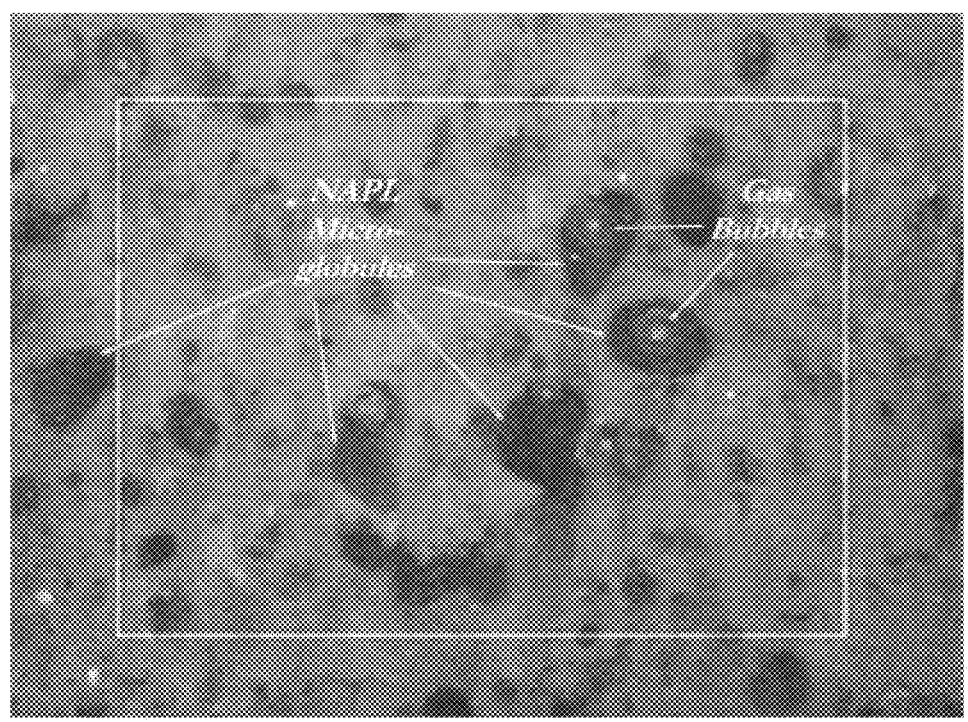
FIG. 3 is an image of a subsurface white-light-only-illuminated image.

FIG. 3 shows an example of a subsurface white-light-only-illuminated image taken at a site that had been contaminated with chlorinated solvents and petroleum products. In the image, the nonaqueous phase liquid (NAPL) appears as dark globules on a light gray soil background. In some situations, the NAPL globules coalesce into "ganglia" type structures. Note that in addition to the microglobules of NAPL the image in FIG. 3 shows what appear to be small gas bubbles entrained in the NAPL globules. Due to the large difference in refractive indexes between the gas and surrounding NAPL phase, the gas bubbles can be distinguished by their high reflectance of the illumination light provided by the white light source 16. The UV-light-only-illuminated image may be used to determine if the gas was generated by microbial degradation. In other words, the UV-light-only-illuminated image may be compared with the white-light-only-illuminated image to determine whether or not natural attenuation is occurring and where it is occurring in the subsurface soil environment 22.

The fluorescence response recorded in the UV-light-only-illuminated image may be used to characterize soil organic matter (SOM), which is the final result of the combined effect of decomposition and humification processes driven by microorganisms on plant and animal residues. The fluorescence spectra provide information on the chemical structure and conformation of the molecules comprising the SOM as well as the biodegradation processes. Bacterial intrinsic fluorescence may be used for identification and characterization purposes as well. The endogenous fluorophores in bacteria include protein tryptophans, other amino acids (tyrosine and phenylalanine), nucleic acids, and co-enzymes. Their excitation maxima lie in the range 250-450 nanometers (nm) (spanning the UV/VIS spectral range), whereas their emission maxima lie in the range 280-540 nm (spanning the UV/VIS spectral range).

Figure 4A:
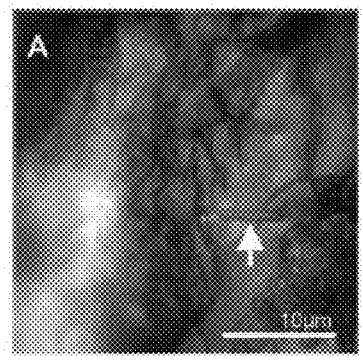
FIGS. 4A-4F are example images that may be captured or created by a fluorescence probe.
Figure 4B:
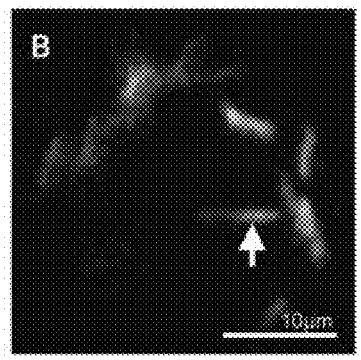
Figure 4C:
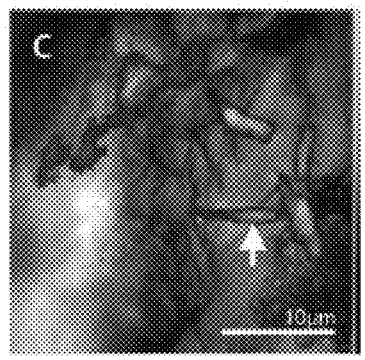
Figure 4D:
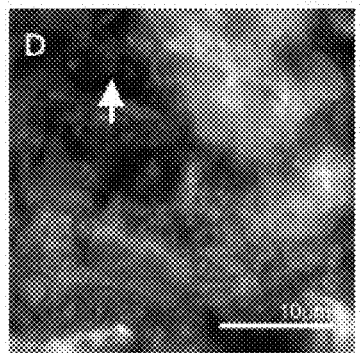
Figure 4E:
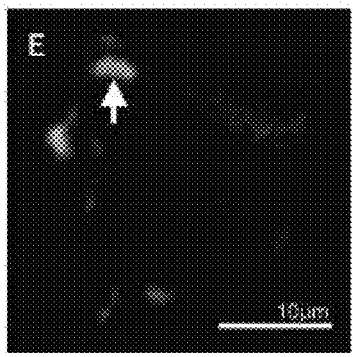
Figure 4F:
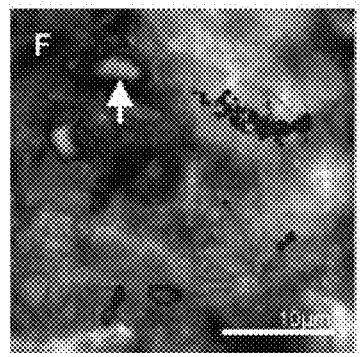

FIGS. 4A and 4D are white-light-only-illuminated images of bacterial cells on siderite and basalt substrates respectively. FIGS. 4B and 4E are UV-light-only-illuminated images of the bacterial cells on siderite and basalt substrates respectively showing the native fluorescence of the bacterial cells. FIG. 4C is an overlay of the UV-light-only-illuminated image 4B over the white-light-only-illuminated image 4A. FIG. 4F is an overlay of the UV-light-only-illuminated image 4E over the white-light-only-illuminated image 4D. In FIG. 4A, the arrow points to a morphology consistent with a bacterium. In FIG. 4B, the native fluorescence shows that the morphology indicated by the arrow in the visible image (i.e., FIG. 4A) is a bacterium with other previously undetected bacterial cells surrounding it. In FIG. 4D, the arrow indicates the location of one of the bacterial cells observed in FIG. 4E. In FIG. 4E, the arrow points to a bacterium whose morphology cannot be seen in the white-light-only-illuminated image. In some of the fluorescence images, speckled features are bacterial cells beyond the depth of focus of the imaging system. In FIGS. 4A-4F, the bacteria were excited by a UV light source of 224 nm. Fluorescence due to siderite and basalt was nonexistent and did not obscure fluorescence from bacterial cell and spores. Consequently, native fluorescence imaging may provide information on both organics and microbial activity, which in turn can be used to assess natural attenuation.

Figure 5A:
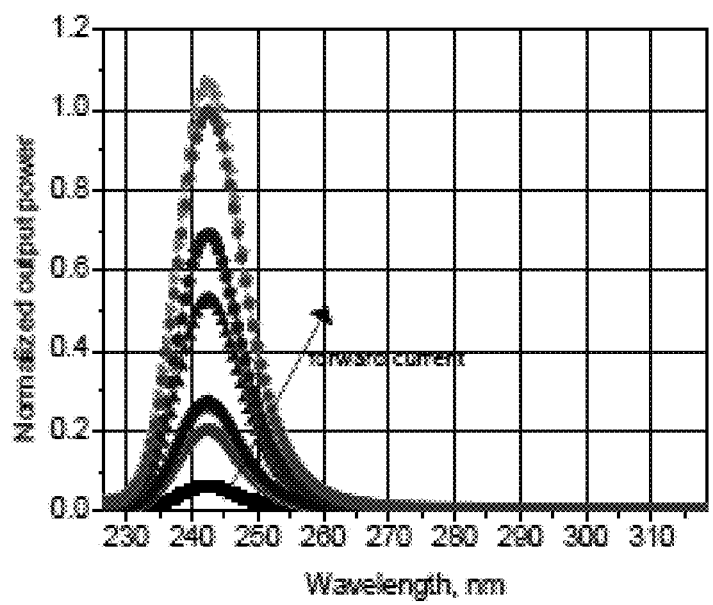
FIGS. 5A-5B are plots of data.

The UV light source 18 may be any light source capable of producing light in the UV spectrum. Suitable examples of the UV light source 18 include, but are not limited to, LEDs and lasers. For example, Sensor Electronic Technology, Inc. offers LEDs that illuminate in the UV spectrum (240-355 nm range). FIG. 5A shows the emission spectrum of a deep UV LED whose peak emission occurs at 245 nm. The full width at half maximum (FWHM) is 12 nm. This wavelength will excite fluorescence from the amino acids tryptophan, tyrosine, and phenylalanine.

Figure 5B:
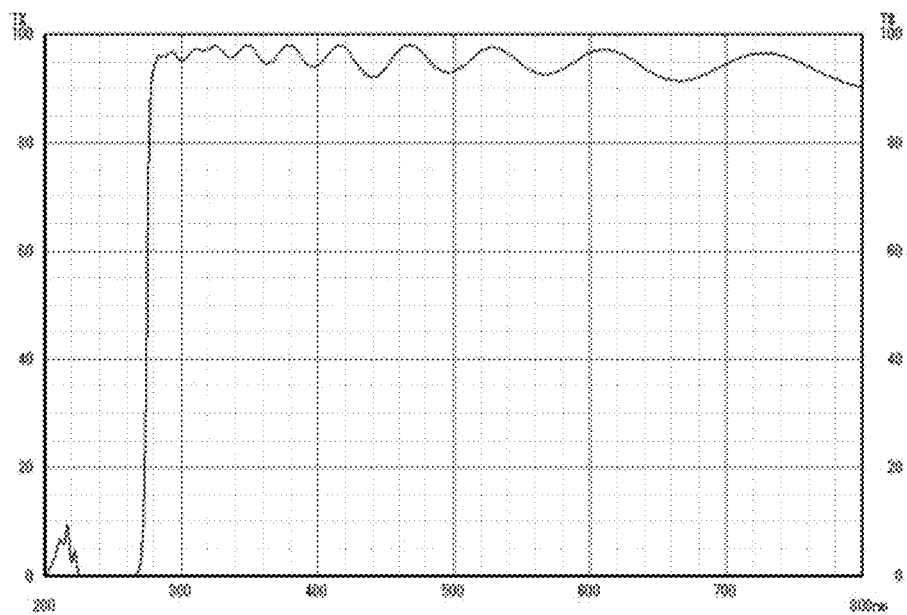

The imaging system 20 may be any optical system capable of capturing visible images of the subsurface soil environment on a scale commensurate with a distribution of microbes and/or minerals that are desired to be studied. In other words, if one desires to study microbes, the imaging system 20 is capable of capturing visible images on the micro scale such that individual microbes may be identified. Such visible images provide information on the biogeochemical and hydrogeological processes that are occurring in the subsurface soil environment 22. Such data can be used to quantify natural attenuation, guide remediation efforts, delineate contaminants in low-permeability zones, determine optimal placement of monitoring wells, and determine where samples should be taken for further chemical analysis. With regards to remediation, the probe could be used to identify active and inactive zones in an aquifer thereby identifying critical regions within a contaminated site where targeted delivery of remediation agents would be beneficial. A suitable example of the imaging system 20 includes, but is not limited to, a charge-coupled device (CCD) camera that operates in the UV spectral range. An example of such a UV-sensitive CCD camera is the CCD camera available from JAI Technologies. The imaging system 20 may also comprise a longpass (LP) filter that may be placed in front of the CCD camera. This LP filter may be used to block the UV excitation while letting the fluorescence emissions through to the CCD camera for imaging. FIG. 5B shows the transmission spectrum of a longpass filter (from Asahi Spectra) that may block the emission of the UV LEDs while transmitting any wavelengths greater than 285 nm. The longpass filter may be selected that only transmits light having a wavelength that is 30-50 nm red-shifted from the wavelength of the UV light source. The imaging system 20 may further comprise optical components for magnification and/or focusing.

The fluorescence probe 10 can perform in-situ, real time, native fluorescence imaging of a soil profile and is configured to obtain visual data, with high vertical and horizontal spatial resolution, that may provide information on both organics and microbial activity. The imaging system 20 may be configured to superimpose the white-light-only-illuminated image and the UV-light-induced-fluorescence image of the subsurface soil environment 22 at the given depth. Examples of such superimposed images are shown in FIGS. 4C and 4F.

Figure 6:
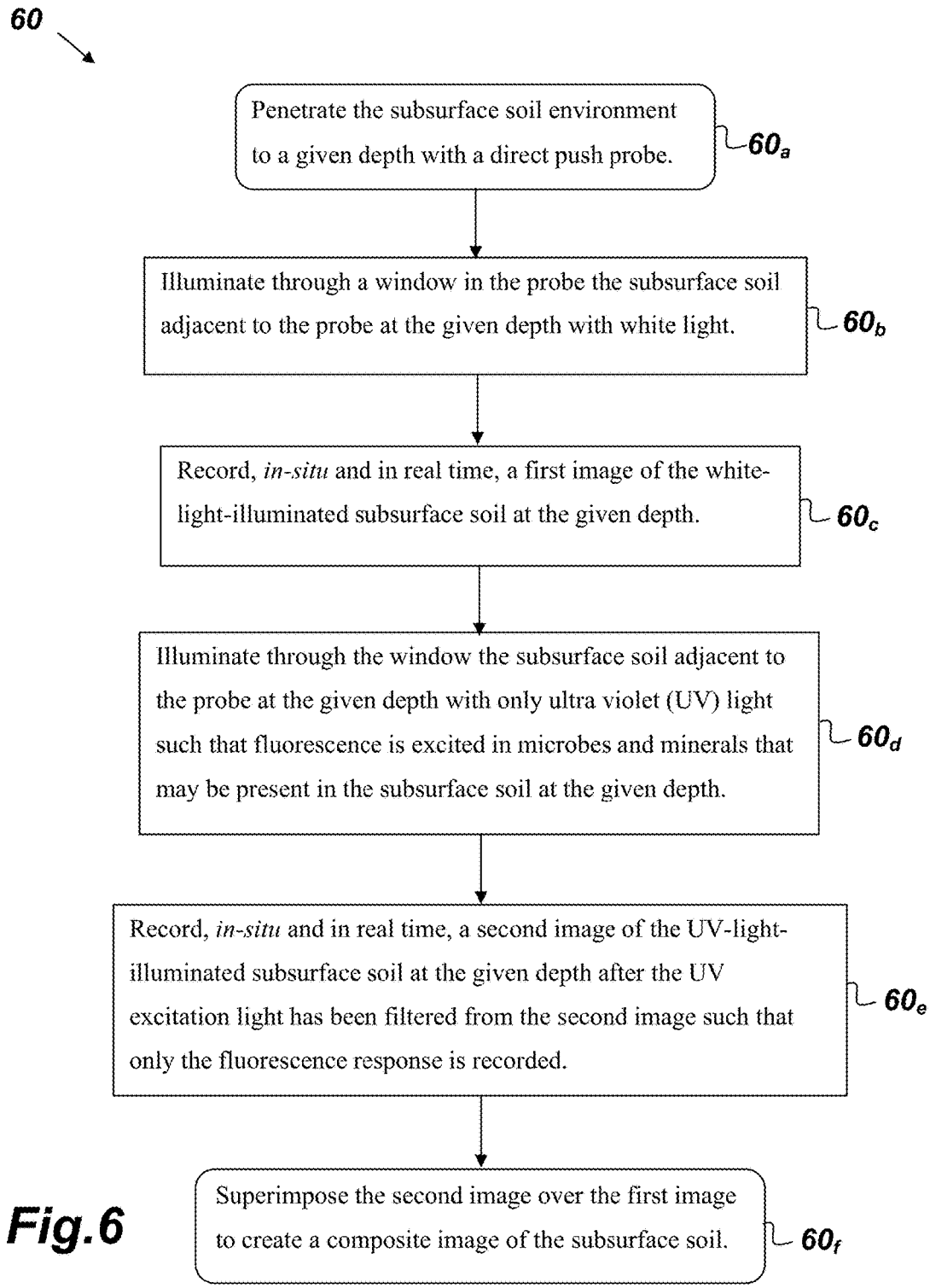
FIG. 6 is a flowchart of a fluorescence imaging method.

FIG. 6 is a flowchart of a method 60 for fluorescence imaging with the fluorescence probe 10. Method 60 comprises the following steps. The first step $60_a$ provides for penetrating the subsurface soil environment 22 to a given depth with a direct push probe 12. The next step $60_b$ provides for illuminating through the window 14 in the probe 12 the subsurface soil adjacent to the probe 12 at the given depth with white light. The next step $60_c$ provides for recording, in-situ and in real time, a first image of the white-light-illuminated subsurface soil at the given depth. The next step $60_d$ provides for illuminating through the window 14 the subsurface soil adjacent to the probe 12 at the given depth with only UV light such that fluorescence is excited in microbes and minerals that may be present in the subsurface soil at the given depth. The next step $60_e$ provides for recording, in-situ and in real time, a second image of the UV-light-illuminated subsurface soil at the given depth after the UV excitation light has been filtered from the second image such that only the fluorescence response is recorded. The next step $60_f$ provides for superimposing the second image over the first image to create a composite image of the subsurface soil.

The probe 12 may be pushed to a plurality of depths at any given location and a separate composite/superimposed image may be created at each depth. The probe may be continuously pushed through the subsurface soil, and the illuminating steps may be performed with rapid sequential flashes of white light and UV light from the white and UV light sources respectively.

From the above description of the fluorescence probe 10, it is manifest that various techniques may be used for implementing the concepts of the fluorescence probe 10 without departing from the scope of the claims. The described embodiments are to be considered in all respects as illustrative and not restrictive. The method/apparatus disclosed herein may be practiced in the absence of any element that is not specifically claimed and/or disclosed herein. It should also be understood that the fluorescence probe 10 is not limited to the particular embodiments described herein, but is capable of many embodiments without departing from the scope of the claims.

We claim:

1. A fluorescence imaging method comprising the following steps:
    penetrating a subsurface soil environment to a given depth with a cone penetration testing (CPT) direct push probe;
    illuminating through a window in the probe the subsurface soil adjacent to the probe at the given depth with white light;
    recording, in-situ and in real time, a first image of the white-light-illuminated subsurface soil at the given depth;
    illuminating through the window the subsurface soil adjacent to the probe at the given depth with only ultra violet (UV) light such that fluorescence is excited in microbes and minerals that may be present in the subsurface soil at the given depth;
    recording, in-situ and in real time, a second image of the UV-light-illuminated subsurface soil at the given depth after the UV excitation light has been filtered from the second image such that only the fluorescence response is recorded;
    superimposing the second image over the first image to create a composite image of the subsurface soil; and
    quantifying a capability of the soil at the given depth to naturally attenuate contaminants;
    assessing and managing a spatial variability of geochemical and microbiological conditions; and
    delineating contaminants in low-permeability zones.

2. The method of claim 1, wherein the first and second images are recorded with a charge-coupled device (CCD) camera.

3. The method of claim 2, wherein the probe is pushed to a plurality of depths at a given location and wherein a separate composite image is created at each depth.

4. The method of claim 3, wherein the probe is pushed at least 2 meters below a soil surface.

5. A fluorescence imaging method comprising the following steps:
    penetrating a subsurface soil environment to a plurality of depths at a given location with a cone penetration testing (CPT) direct push probe;
    illuminating through a window in the probe the subsurface soil adjacent to the probe at the given depth with white light;
    recording, in-situ and in real time, a first image of the white-light-illuminated subsurface soil at the given depth;
    illuminating through the window the subsurface soil adjacent to the probe at the given depth with only ultra violet (UV) light such that fluorescence is excited in microbes and minerals that may be present in the subsurface soil at the given depth;
    recording, in-situ and in real time, a second image of the UV-light-illuminated subsurface soil at the given depth after the UV excitation light has been filtered from the second image such that only the fluorescence response is recorded, wherein the first and second images are recorded with a charge-coupled device (CCD) camera;
    superimposing the second image over the first image to create a composite image of the subsurface soil, wherein a separate composite image is created at each depth; and
    determining biogeochemical processes that are occurring in the subsurface soil at each of the plurality of depths based on the composite image taken at each depth.

6. The method of claim 2, wherein the UV excitation light is filtered from the second image by a longpass optical filter before the second, induced fluorescence image is recorded by the CCD camera.

7. The method of claim 3, wherein the composite images are created at a spatial scale commensurate with a distribution of contaminants that are desired to be studied.

8. The method of claim 1, further comprising the step of determining where natural attenuation of contaminants is occurring in the soil.

9. The method of claim 7, wherein the probe is continuously pushed through the subsurface soil, and wherein the illuminating steps are performed with rapid flashes of white light and UV light.

* * * * *